United States Patent [19]
Calvert

[11] 4,430,615
[45] Feb. 7, 1984

[54] REFLECTION TYPE PROBES FOR EDDY CURRENT TESTING INSTRUMENTS

[75] Inventor: John H. Calvert, Hertfordshire, England

[73] Assignee: Hocking Electronics Limited, Great Britain

[21] Appl. No.: 292,628

[22] Filed: Aug. 13, 1981

[30] Foreign Application Priority Data

Aug. 23, 1981 [GB] United Kingdom ............... 8027498

[51] Int. Cl.³ ............... G01N 27/72; G01R 33/12; H01F 27/28; H01F 27/38
[52] U.S. Cl. ................... 324/239; 324/241; 336/212; 336/221; 336/226
[58] Field of Search ................ 324/236–243, 324/262; 336/212, 226, 221

[56] References Cited

U.S. PATENT DOCUMENTS 2,994,034  7/1961  Kinzer ........................... 324/239
4,223,360  9/1980  Sansom et al. ............... 336/226 X

*Primary Examiner*—Gerard R. Strecker
*Assistant Examiner*—Warren S. Edmonds
*Attorney, Agent, or Firm*—Hayes, Davis & Soloway

[57] ABSTRACT

A reflection type probe for an eddy current testing instrument comprises a ferromagnetic core 2, 3 and a driver coil system 8 and a pick-up coil system 9 mounted on the core, the core having four limbs 4 to 7 each with a free end. One of the coil systems 9 is wound on the four limbs with its turn equally distributed between the four limbs and the other coil system 8 is wound on a core part remote from the turns of the coil system 9 and which interconnects the core limbs at least in pairs. Advantageously the coil system which is wound on the limbs 4 to 7 is the pick-up coil system. A detector coil section of the pick-up coil system can then have its turns equally distributed between one pair of limbs and a balancing coil section having its turns equally distributed between the other pair of limbs. In further development of this arrangement, the opposed winding of the two coil sections can be readily achieved by "Figure of 8" windings around pairs of the limbs, one half of each "Figure of 8" forming a turn of the detector coil section and the other half forming a turn of the balancing coil section.

6 Claims, 1 Drawing Figure

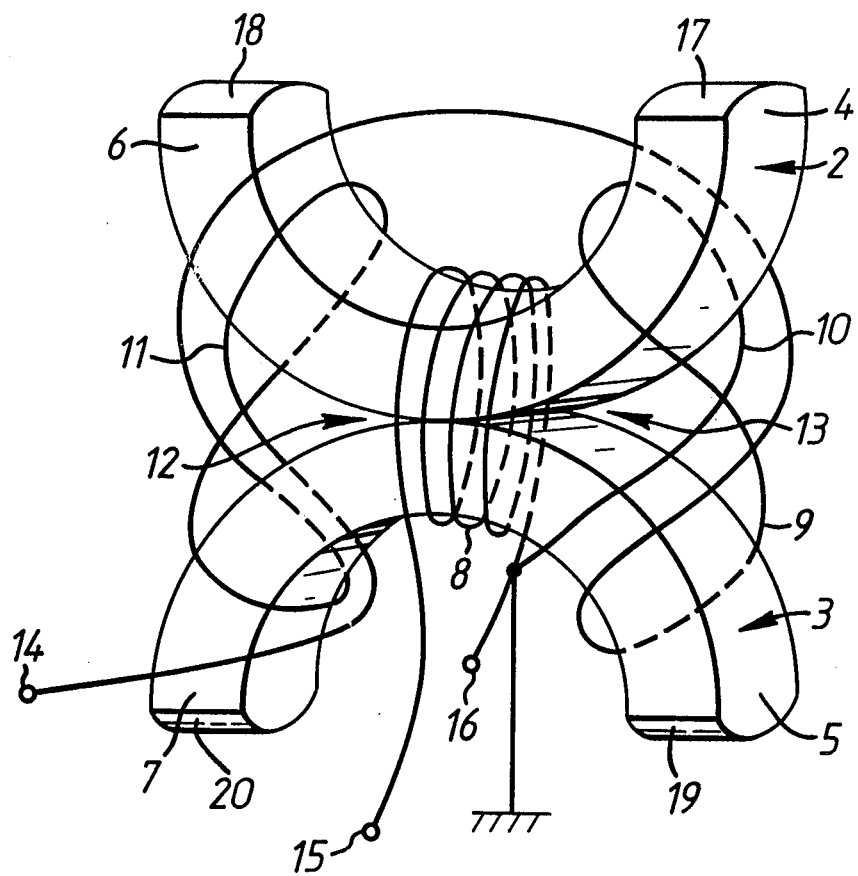

REFLECTION TYPE PROBES FOR EDDY CURRENT TESTING INSTRUMENTS

BACKGROUND OF THE INVENTION

This invention relates to reflection type probes for use with eddy current testing instruments. Such instruments, as is well known, are used for a variety of purposes involving non-destructive testing, such as crack detection and conductivity and thickness measurements, in bodies of electrically conducting material.

Reflection type probes comprise basically a former on which are mounted a driver coil system energised from an alternating current supply and a pick-up coil system which generates an e.m.f. as a result of its coupling with the driver coil system through the alternating magnetic field generated by the driver coil system. The former may be of ferromagnetic material or the coil systems may be air cored. When the probe is brought adjacent an electrically conducting body, eddy currents generated in the body modify the electromagnetic field and produce a change in amplitude and phase of the generated e.m.f. Both the amplitude of the generated e.m.f. and the phase relationship with the driving signal varies in dependence upon the proximity of the probe to the electrically conducting body, i.e. they are sensitive to so-called lift-off. However the output from the coil systems is connected to appropriate electronic circuits which operate so as to keep the phase relationship sensibly constant. For this reason the instruments wih which the probes are used are usually designed tomeasure phase-shift when performing their testing function.

Probe designs are known in which the pick-up coil system is in two opposingly wound coil sections so that in air the e.m.fs generated across the two coil sections cancel each other out. In use of such a probe one of the coil sections becomes disposed nearer to the body to be tested than the other and serves as the detector coil section sensitive to the eddy currents generated in the body. The other coil section is not significantly influenced by the eddy currents but will be subjected, in theory at least, to the same extraneous influences as the detector coil section. The e.m.fs generated in the two coil sections as a result of extraneous influences will therefore cancel each other out so that in theory the effect of extraneous influences on the pick-up coil system will be nullified. For convenience the other coil section of the pick-up coil system will be referred to as a "balancing coil section".

SUMMARY OF THE INVENTION

In one embodiment of the probe design in which the pick-up coil system has opposingly wound detector coil and balancing coil sections, a pot core has been used with the driver coil system surrounding the two pick-up coil sections which are spaced from each other axially of the pot core. In use the end face of the pot core adjacent the detector coil section is placed in proximity to or in contact with the body to be tested.

In practice it has so far proved extremely difficult to provide an accurately balanced pick-up coil system because of physical and/or electromagnetic asymmetry between the two pick-up coil sections. The object of the present invention is to provide a probe design in which an accurate balance can be more readily and reliably achieved than hitherto.

According to the present invention a reflection type probe for an eddy current testing instrument comprises a ferromagnetic core and a driver coil system and a pick-up coil system mounted on the core, said core having four limbs each with a free end, one of said coil systems being wound on the four limbs with its turns equally distributed between the four limbs and the other coil system being wound on a core part remote from the turns of said one coil system and which interconnects the core limbs at least in pairs. Thus said core may comprise an "H" core with the cross limb of the "H" constituting said core part. Alternatively said core may be formed by two back to back 'C' or 'U' core members, the adjoining parts of said 'C' or 'U' core members constituting said core part.

With a probe according to the invention it is at least ensured that there is no differential coupling between the driver and pick-up coil systems. This contrasts with the above described known probe design where the turns of the pick-up coil system couple more closely with certain turns of the driver coil system than other turns, because of the relative dispositions of the turns of the two coil systems.

Advantageously the coil system which is wound on said four limbs is the pick-up coil system. A detector coil section of the pick-up coil system can then have its turns equally distributed between one pair of limbs and a balancing coil section having its turns equally distributed between the other pair of limbs. In further development of this arrangement, the opposed winding of the two coil sections can be readily achieved by "Figure of 8" windings around pairs of the limbs. Thus in each "Figure of 8" one half forms a turn of the detector coil section and the other half forms a turn of the balancing coil section. Hence the effects of any change of characteristics along the length of the wire forming the coil turns are minimised.

The "Figure of 8" windings have great practical advantage in that it is ensured automatically that the detector coil section and the balancing coil section have the same number of turns. Also where the core limbs are curved, as in the case of back to back 'C' core members, the winding arrangement is very compact since the winding turns fill the external cusps provided in core.

There are normally three terminals connecting the coil systems of a probe to the testing instrument, namely an input terminal at one end of the driver coil system, an output terminal at one end of the pick-up coil system and a common (earth) terminal at the other ends of the coil systems. With a probe in accordance with the invention both coil systems can be wound from a single length of wire, by first winding one coil system and then winding the other coil system and then simply making a tapping between the coil systems to form the common terminal, the two ends of the wire providing said input and output terminals.

Conveniently the free ends of the pair of core limbs carrying the detector coil section can be profiled to fit intimately the contour of a body to be tested. This is very difficult and size limiting with probes in which pot cores or air cored coils are used.

BRIEF DESCRIPTION OF THE DRAWING

One probe construction in accordance with the invention will now be described by way of example with reference to the accompanying drawing which shows a perspective view of the probe.

DETAILED DESCRIPTION OF THE PREFERRED EMBODIMENT

The probe has a ferromagnetic core comprising two semitoroids 2 and 3 of ferrite material disposed back to back and bonded together where they adjoin. Thus the core has four limbs 4 to 7 each with a free end.

Wound on the core over adjoining parts of the two semitoroids is a driver coil system 8 and distributed over the four limbs is a pick-up coil system 9. The coils are wound from a single length of wire by first winding the pick-up coil system 9 is a first "Figure of 8" configuration 10 over the limbs 4 and 5 and then in a second "Figure of 8" configuration 11 over the limbs 6 and 7. Thus the turns on the limbs 4 and 5 are opposingly wound and similarly the turns of the limbs 6 and 7 are opposingly wound. However the turns on the limbs 4 and 6 are wound in the same sense and together constitute the detector coil section of the pick-up coil system and the turns on the limbs 5 and 7 are wound in the same sense and together constitute the balancing coil section of the pick-up coil system. The driver coil system 8 is then wound. For clarity, only a few turns of the coil systems 8 and 9 are shown wound on the core. In practice the number of turns would be much greater, and the "Figure of 8" windings of the pick-up coil system 9 would fill the external cusps 12 and 13 defined between the two semitoroids.

The probe has an output terminal 14 at one end of the pick-up coil system 9. The terminal 14 is formed by the end of the length of wire constituting the start of the winding of the pick-up coil system. The probe also has an input terminal 35 at one end of the driver coil system 8. The terminal 15 is formed by the end of the wire remaining after winding the driver coil system 8. The probe also has a common terminal 16 at the other ends of the two coil systems formed by a tapping of the wire at the transition from the winding of the pick-up coil system to the winding of the driver coil system.

In use of the probe the free ends of the limbs 4 and 6 would be brought into contact or proximity with a body to be tested and traversed over and along a predetermined path of the body. It is often the case that the probe has to move over a profiled part of the body, for example along a groove or channel having a curved cross-section. Advantageously the surfaces at the free ends of the limbs 4 and 6 can be shaped to intimately fit the profile. As shown by way of example in the drawings these end surfaces 17 and 18 are curved to fit such a groove or channel and the probe is then moved along the channel with one of the limbs 4 and 6 ahead of the other. Any such profiling may be accomplished without affecting the balance of the system providing that a similar amount of material is removed from the limbs 5 and 7. This is achieved in this example by providing the end surfaces 19 and 20 of the limbs 5 and 7 with a similarly curved profile.

What is claimed is:

1. A reflection type probe for use with an eddy current testing instrument, said probe comprising a ferromagnetic core, a driver coil system and a pick-up coil system, both of said systems being mounted on the core, said core having four limbs each with a free end, one of said coil systems being wound on the four limbs with its turns equally distributed between the four limbs and the other coil system being wound on a part of the core remote from the turns of said one coil system and which interconnects the core limbs at least in pairs.

2. A reflection type probe according to claim 1, wherein the coil system wound on said four limbs is the pick-up coil system, whereby a detector coil section is provided on two of said limbs and a balancing coil section is provided on the other two of said limbs.

3. A reflection type probe according to claim 2, wherein said pick-up coil system comprises "Figure of 8' windings around pairs of the limbs, one half of each "Figure of 8" forming a turn of the detector coil section and the other half forming a turn of the balancing coil section.

4. A reflection type probe according to claim 3, wherein said core limbs are curved to provide external cusps between pairs of the limbs, the cross-over portions of the "Figure of 8" winding being disposed in said cusps.

5. A reflection type probe according to claim 1 and having an input terminal at one end of the driver coil system, an output terminal at one end of the pick-up coil system and a common terminal at the other end of the coil systems, wherein said coil systems are wound from a single length of wire, the ends of the wire providing said input and output terminals and a tapping on the wire providing said common terminal.

6. A reflection type probe according to claim 2, wherein the free ends of the two limbs carrying the detector coil section are curved.

* * * * *